(12) United States Patent
Kuhfuß et al.

(10) Patent No.: US 12,115,013 B2
(45) Date of Patent: Oct. 15, 2024

(54) DEVICE FOR HOLDING A STORAGE MEDIUM

(71) Applicant: Dürr Dental SE, Bietigheim-Bissingen (DE)

(72) Inventors: Andreas Kuhfuß, Ludwigsburg (DE); Enes Mustajbegovic, Bietigheim-Bissingen (DE)

(73) Assignee: Dürr Dental SE, Bietigheim-Bissingen (DE)

( * ) Notice: Subject to any disclaimer, the term of this patent is extended or adjusted under 35 U.S.C. 154(b) by 130 days.

(21) Appl. No.: 18/058,257

(22) Filed: Nov. 22, 2022

(65) Prior Publication Data

US 2023/0172569 A1    Jun. 8, 2023

(30) Foreign Application Priority Data

Nov. 15, 2021    (DE) ...................... 10 2021 129 771.0

(51) Int. Cl.
*A61B 6/51*    (2024.01)

(52) U.S. Cl.
CPC .................................. *A61B 6/512* (2024.01)

(58) Field of Classification Search
CPC ...... A61B 6/512; A61B 6/4283; G03B 42/042
See application file for complete search history.

(56) References Cited

U.S. PATENT DOCUMENTS

| 5,737,388 A | * | 4/1998 | Kossila ................ A61B 6/4435 |
| | | | 378/170 |
| 6,540,399 B1 | * | 4/2003 | Eppinger ................. A61B 6/51 |
| | | | 378/170 |
| 7,033,075 B2 | | 4/2006 | Landis et al. |
| 2004/0170253 A1 | | 9/2004 | Landis et al. |
| 2005/0053199 A1 | | 3/2005 | Miles |
| 2017/0202526 A1 | | 7/2017 | Palermo |

FOREIGN PATENT DOCUMENTS

| DE | 8610962 U1 | 6/1986 |
| DE | 19581556 T1 | 3/1997 |
| EP | 0314506 A1 | 5/1989 |
| WO | 2010/138684 A1 | 12/2010 |
| WO | 2018/022564 A1 | 2/2018 |

OTHER PUBLICATIONS

Office Action mailed Jul. 15, 2022 in connection with German Patent Application No. 102021129771.0, 5 pgs.
European Search Report mailed Mar. 16, 2023 in connection with European Patent Application No. 22207332.2, 9 pgs.

* cited by examiner

*Primary Examiner* — Edwin C Gunberg
*Assistant Examiner* — Mamadou Faye
(74) *Attorney, Agent, or Firm* — Chiesa Shahinian & Giantomasi PC

(57) ABSTRACT

The invention relates to a device for holding a storage medium in the oral cavity of a patient for at least one X-ray exposure.

15 Claims, 8 Drawing Sheets

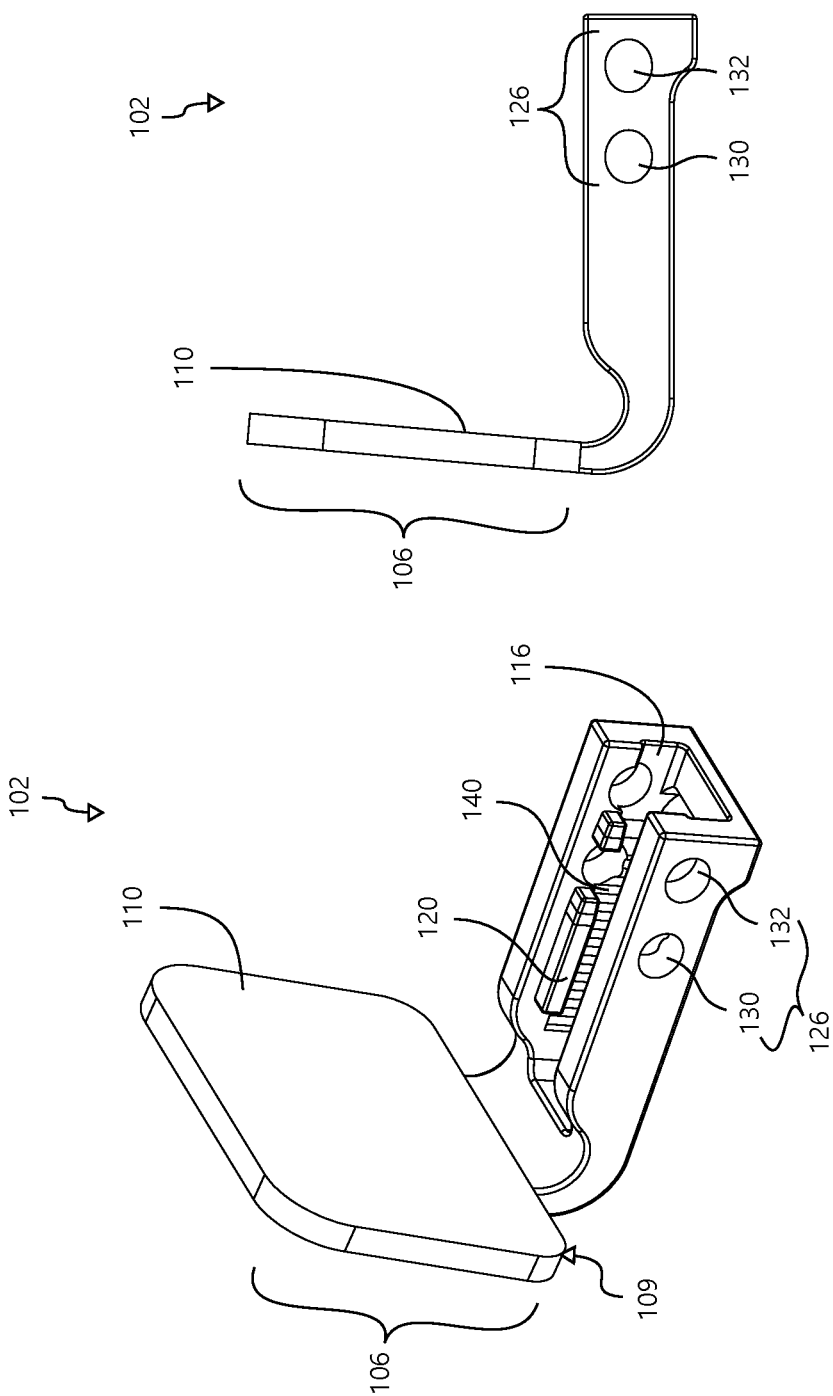

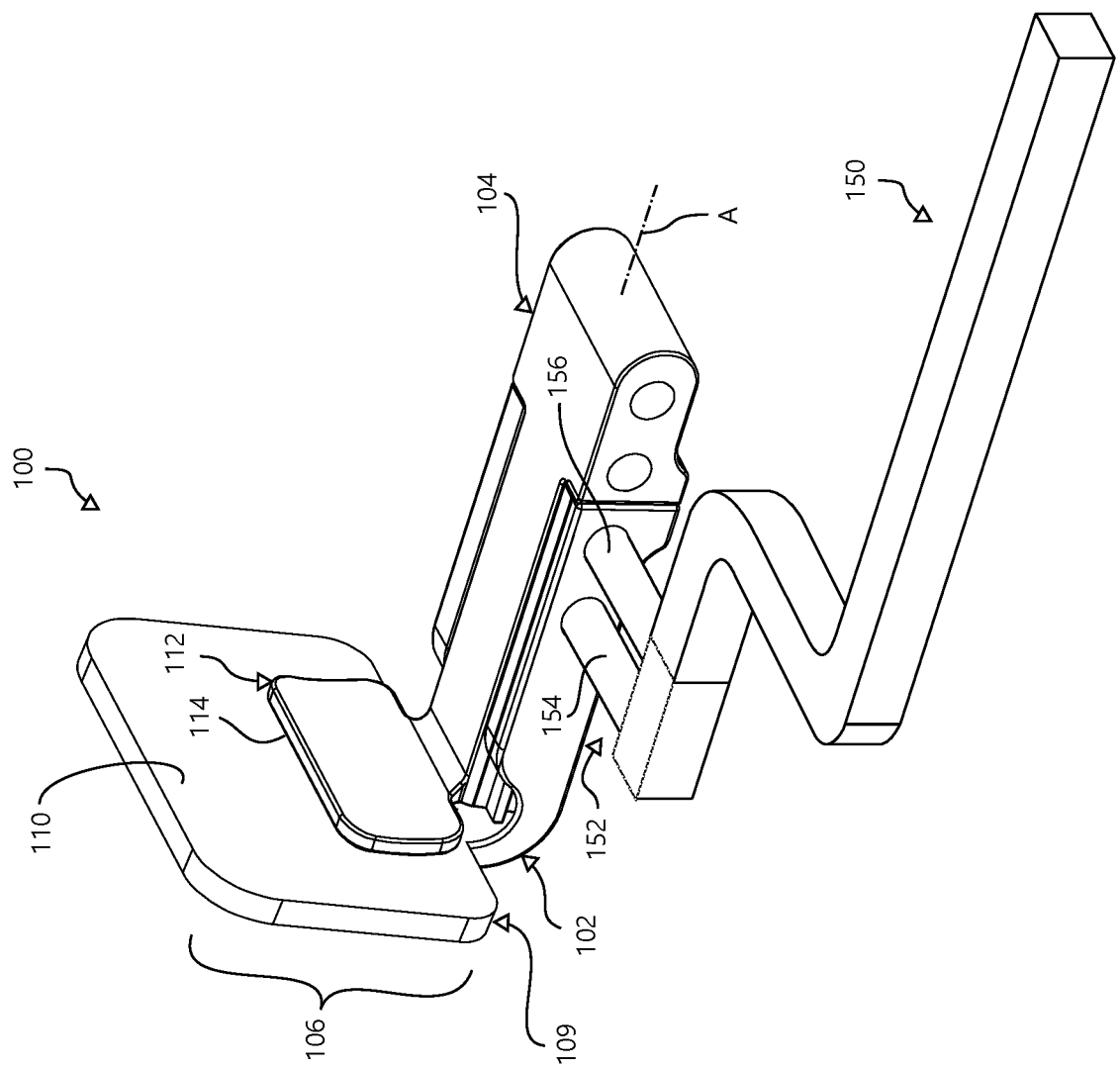

DEVICE FOR HOLDING A STORAGE MEDIUM

CROSS-REFERENCE TO RELATED APPLICATIONS

This application claims the benefit of priority from German Patent Application No. 102021129771.0, filed Nov. 15, 2021, the disclosure of which is incorporated herein by reference in its entirety.

FIELD

The invention relates to a device for holding a storage medium in the oral cavity of a patient for at least one X-ray exposure, the device comprising a holding portion and a bite portion.

BACKGROUND

Such devices are components of holding systems for imaging plates. The purpose of such holding systems is to align and hold an imaging plate in the patient's oral cavity to an X-ray device.

In addition to the device for holding an imaging plate with a plate holding portion and a bite portion, the usual design of such a holding system also includes a guide rod which can be attached to the device and which can also have a sighting ring on a side facing away from the holding device. By means of the guide rod and, if applicable, the sighting ring, the alignment of the X-ray device as well as the distance can be adjusted.

To take an X-ray exposure, the holding device is inserted into the patient's mouth. The patient bites down on the bite portion of the holding device to fix it in place, so that the holding system remains held and aligned by the pressure built up by the jaw as the patient bites down.

Storage media such as imaging plates are used in the dental field for different exposure areas and requirements such as anterior tooth exposures, bite wing exposures, etc. in different sizes. The actual so-called intraoral storage medium is located in a protective cover during the X-ray exposure, which protects it from light incidence and/or possible contamination.

For example, the imaging plate is separated from the protective cover for reading out the image data in a scanner. After completion of the image information evaluation, the imaging plate is erased and then reinserted into a new hygienic protective sleeve: the sleeve already in use is disposed of. Due to the repeated insertion and removal of the imaging plate into/from the sleeve or envelope, there must be a certain distance between the imaging plate and the sleeve or between the storage medium in general and its envelope. This complicates the exact positioning of the imaging plate by means of the existing holding systems.

WO 2018/022564 describes, among other things, a holder for an imaging plate. The holder has a bite block and a support plate arranged at right angles to it. The support plate has spring arms which tighten a band attached to an imaging plate sleeve and thus attract the imaging plate to the support plate.

A disadvantage of this retaining system is that an additional retaining band is required on the protective imaging plate sleeve. This means an additional production step and thus increases the manufacturing costs. In addition, the retaining tape can be stretched or overstretched and tear, so that the cover has to be changed and the imaging plate re-placed, which ultimately leads to more expense. Apart from this, the tape pulls when stressed in the area of the seam on the sides of the film forming the envelope. The tensile force of the tape can thus damage the seam, which can lead to undesirable contamination.

DE 8610962 describes a retaining system which has a bite plate and a back plate arranged at right angles to the bite plate. The back plate is curved in the shape of an arc on the upper side and engages over a dental film inserted on it. Opposite on the underside is a resilient clamping strip, by means of which a clamping action is exerted on an inserted dental film. When a dental film is inserted, it has to be bent comparatively strongly. In addition, the clamping force of the clamping strip is fixed and cannot be released, for example, for inserting or removing the tooth film.

U.S. Pat. No. 7,033,075 describes a holding system in which two jaws are attached to a bite block, between which a sensor can be clamped. The jaw facing away from the bite block can be adjusted relative to the other jaw by means of a screw and thus the contact pressure on the sensor can be produced and set. A disadvantage of this embodiment is the complex design of the mechanism and the associated difficulty in disinfection. In addition, this design is only suitable for fixed sensors as opposed to imaging plates, since the imaging plate could be damaged by the contact pressure that has to be applied manually.

WO 2010/138684 A1 also describes a holding system for sensors and not for imaging plates, which has two clamping jaws connected by a rubber band, between which a storage sensor is arranged. This device is also not suitable for imaging plates, since imaging plates do not have the rigidity required for this type of mounting.

SUMMARY

It is an object of the invention to disclose a device for holding a storage medium in the oral cavity of a patient, which device is easy to disinfect and provides a secure and gentle holding of the storage medium as well as some convenience for the patient. In particular, it is desirable if a defined clamping force can be applied to the storage medium during the X-ray exposure process, but the clamping force can be removed or at least reduced for loading the storage medium into the holder. Unloading of the imaging plate can be performed in the closed state by overcoming the clamping force applied to the imaging plate.

The task is solved by a device according to the independent claim. Further embodiments of the invention are given in the dependent claims.

The device according to the invention for holding a storage medium in the oral cavity of a patient for at least one X-ray exposure has a holding section and a bite block section, a first part with an abutment region for the storage medium, a first guiding or/and articulation region and a first locking region, and a second part with a clamping region, a second guiding or/and articulation region corresponding to the first guiding or/and articulation region and a second locking region. The abutment region and the clamping region cooperate to form the holding portion. The first and second guide or/and hinge portions cooperate such that the first part and the second part are movable relative to each other between an open position and a clamping position. In the clamping position, a clamping force can be applied or applied to a storage medium located between the contact area and the clamping area. The first part and the second part are lockable relative to each other in the clamping position via a cooperation of the first and the second locking areas.

By virtue of its design, the device according to the invention has several advantages. By means of the mutually corresponding and cooperating guide or/and joint areas, a relative movement can take place in a guided manner, so that the clamping force exerted on a storage medium is applied in the clamping position and is not applied or is applied only with a low clamping force in the open position. This enables safe and, if necessary, single-handed insertion or removal of the storage medium in the holding portion of the device. The locking feature, which fixes the first part and the second part in the clamping position relative to each other, allows a predetermined clamping force to be applied to the storage medium. This minimizes the effects of errors during the creation of an X-ray image, which could occur due to incorrect positioning or local damage to the storage medium in the clamping region. The two-part design may provide for the parts to be separable from one another, thereby making them easily accessible for sterilization.

In one embodiment of the invention, the holding portion may include ergonomic portions that allow the first part to be securely held between a user's index and middle fingers, wherein by means of, again, ergonomic abutment of a user's thumb, the device may be placed in the clamping position.

In a further embodiment of the invention, it is provided that the abutment region has a substantially planar abutment surface for planar support of a storage medium. The contact surface thus supports a kink-free and curvature-free positioning of the storage medium during the X-ray exposure.

The clamping force acting on the storage medium is preferably applied linearly by the shaping of the clamping region, which advantageously allows the storage medium to be easily detached from the holding device without having to completely dismantle it at this time. The holding device can be temporarily stored in a container after the X-ray exposure has been performed and the storage medium has been removed, and can be disassembled for disinfection at a later time.

Advantageously, it can be provided that the contact surface for the storage medium is arranged at an angle of between 75° and 95°, preferably between 80° and 90° to the bite portion. A pre-inclination of between 80° and 90° supports positioning of the storage medium as close as possible to the area to be X-rayed. This can be, for example, in a non-exhaustive list, a tooth region, a jaw region or an implant region. In a preferred embodiment, a detent can be provided, for example a detent pin engaging in a gear wheel, which permits individual adjustability of the inclination of the contact surface for the desired exposure.

In a further embodiment of the invention, it may be provided that the inclination of the retaining portion is adjustable and lockable with respect to the bite portion. Thus, an individual adjustment of the angle of inclination between the holding section and the bite portion can be made and the holding device can be better adapted to the conditions in the oral cavity.

Preferably, the inclination can be arranged or/and adjusted at an angle between 75° and 95°, preferably between 80° and 90°, to the bite portion.

In a further preferred embodiment, recesses corresponding to one another are arranged on the first part and the second part in the locking area in such a way that a locking device can be inserted through the recesses and thus the first part and the second part can be locked to one another. Preferably, the recesses are of the same or very similar dimensions for this purpose and are aligned with one another for the locking operation. The locking device may, for example, be sections of a target rod. In this way, the holding device can be locked or arrested in the clamping position.

A defined force can be applied from the clamping region to the abutment region by means of the retaining device, thus generating a predetermined clamping force. The clamping force generated in this way is the force that must be applied to pull out a storage medium held by the holding device without releasing the clamping position. In one embodiment, for example, this clamping force can be in the range from 1.8 N to 4.2 N, preferably in a range between 2.2 N and 3.4 N, and particularly preferably in a range between 2.5 N and 3.0 N. A clamping force in this range reliably prevents the storage medium from shifting or falling out. As described above, the storage medium (with an envelope such as an enveloping protective film or a protective tube) can be pulled out of the holding device after an X-ray exposure has been performed by overcoming the clamping force, for example for reading out the stored (image) data, without disassembling the holding device or releasing the clamping position.

A number of factors influence the actual level of clamping force: For example, moisture in the oral cavity applied to the surfaces of the storage medium or the enclosure, the abutment region or/and the clamping region during insertion or/and during X-ray exposure can change the surface friction: the force applied by the holding device to the storage medium in the clamping position can vary due to manufacturing tolerances or be changed by material fracture or/and material stretching during operation.

Also, the amount of the clamping force during a measuring process can be influenced by the speed of the extraction and the slip or/and deformation slip that takes place, as well as by partial sliding.

In one embodiment, the locking device comprises an aiming device for aligning an X-ray device.

In another embodiment, the guide region comprises a ledge guide configured to allow the abutment region and the clamping region to slide relative to each other, thereby allowing the clamping force to be applied from the clamping region to the abutment region, particularly with a storage medium located therebetween. The ledge guide can be designed, for example, as a groove ledge guide. Such a ledge guide is technically simple to implement, allows easy separation of the first part and the second part for sterilization purposes, and also allows easy one-handed operation of the device.

As an alternative to the relative displaceability of the abutment region and clamping portion, the hinge region on the first or the second part can have an axis of rotation and a corresponding bearing on the other part.

Preferably, the axis of rotation is arranged in such a way that the abutment region and the clamping portion perform a pivoting movement relative to each other. This also enables the realization of a clamping and open position. In combination with a fixing of the two parts relative to each other in the locking area, a defined contact force of 1.8 N to 4.2 N, preferably in a range between 2.2 N and 3.4 N and particularly preferably in a range between 2.5 N and 3.0 N on the storage medium as well as a removal of the storage medium by overcoming the clamping force, as already described above, can thus also be realized.

Overall, it is advantageous if there is a distance between the abutment region and the clamping portion which is dimensioned such that a storage medium can be introduced between the abutment region and the clamping portion in the open position and a predetermined clamping force is exerted on the storage medium in the clamping position.

In one embodiment, the distance between the abutment region and clamping portion can be varied depending on the storage medium to be introduced.

At the same time or alternatively, the applied clamping force can be variable, for example in the previously mentioned areas. The realization of the necessary clamping force as well as the fixing of the device is ensured by the locking areas arranged according to the invention, in which the locking device can be inserted in dependence on the size of the storage medium.

In the context of the application, the term storage medium is primarily intended to include an imaging plate and the protective sleeve in which the imaging plate for at least one X-ray image is located. However, depending on the present embodiment, an application of the invention to a memory chip, a memory sensor and a memory film as well as, if applicable, additionally the respective protective envelope shall also be included in the scope of protection.

BRIEF DESCRIPTION OF THE DRAWINGS

In the following, embodiments of the invention are explained in more detail with reference to the drawings. In these show:

FIGS. 4, 5 a perspective and a side view of the base part of the storage medium holder of FIGS. 1-3:

FIG. 8 a perspective view of the first embodiment in a clamped position with an attached locking device:

DETAILED DESCRIPTION

First Embodiment

Figure 1:
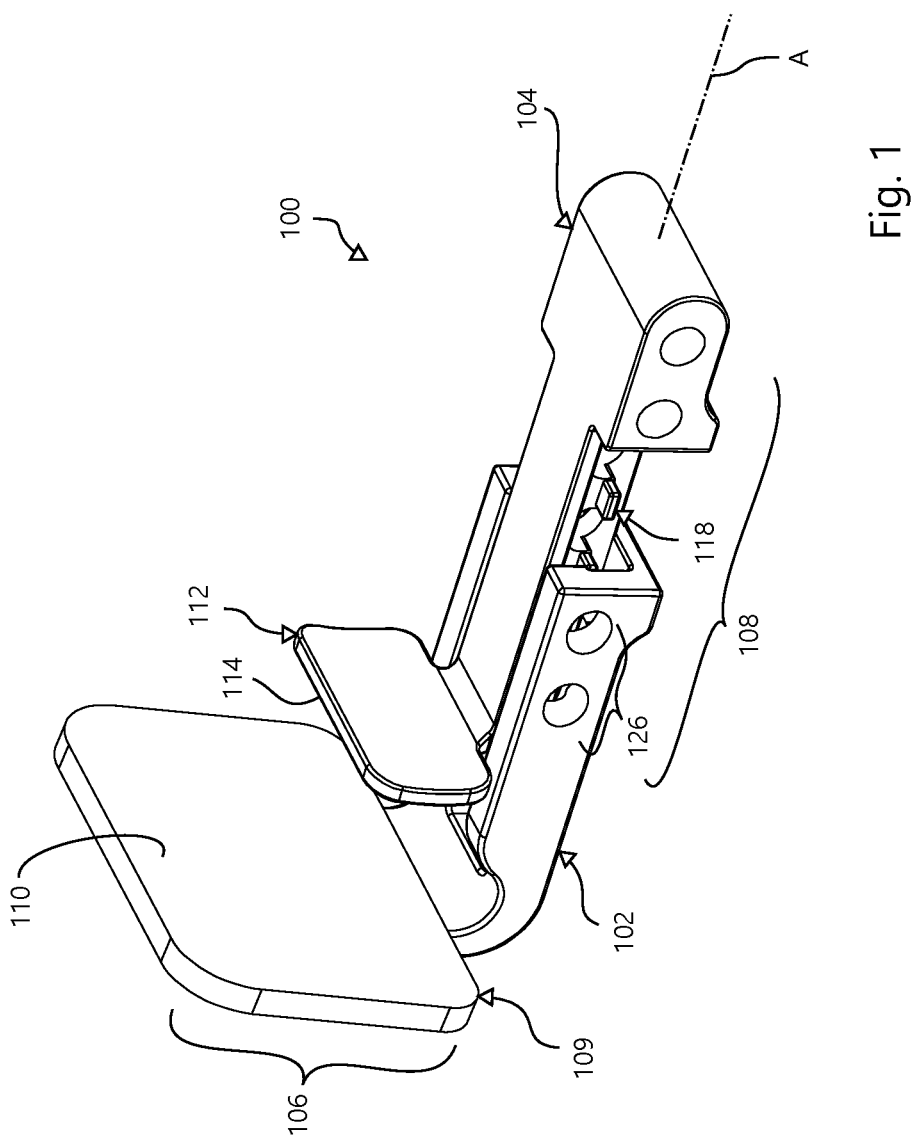
FIG. 1 a perspective view of a first embodiment of a storage medium holder with base part and sliding part in an open position.
Figure 2:
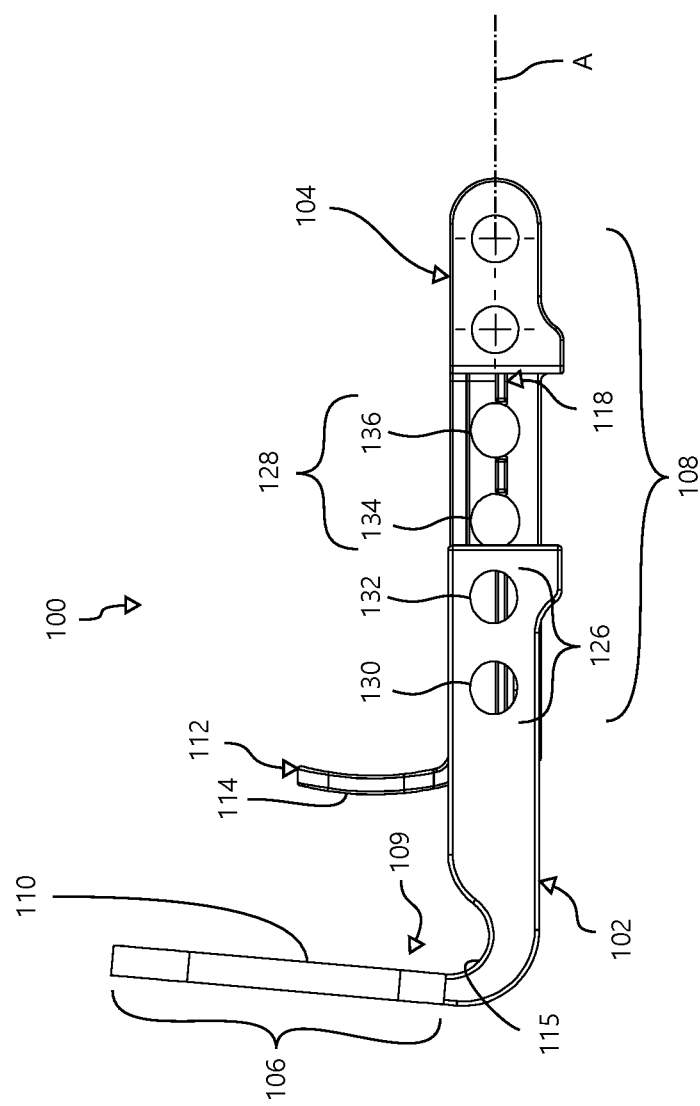
FIG. 2 a side view of the embodiment of FIG. 1.
Figure 7:
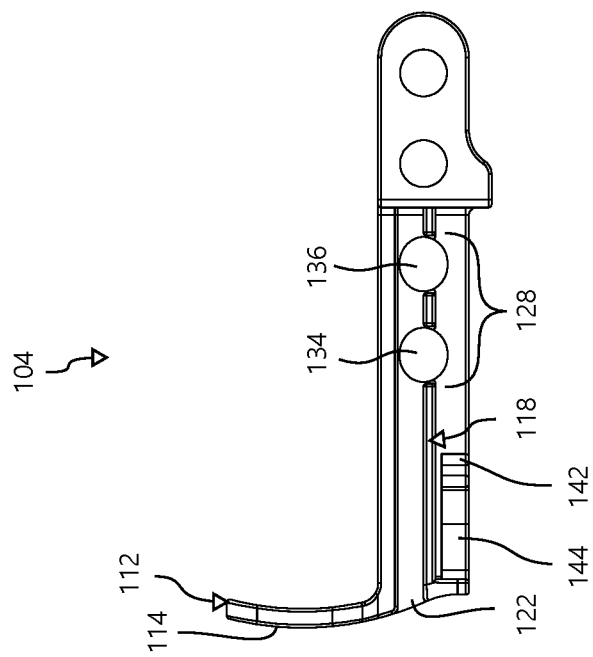
FIGS. 6, 7 a perspective and a side view of the sliding part of the storage medium holder of FIGS. 1-3.
Figure 6:
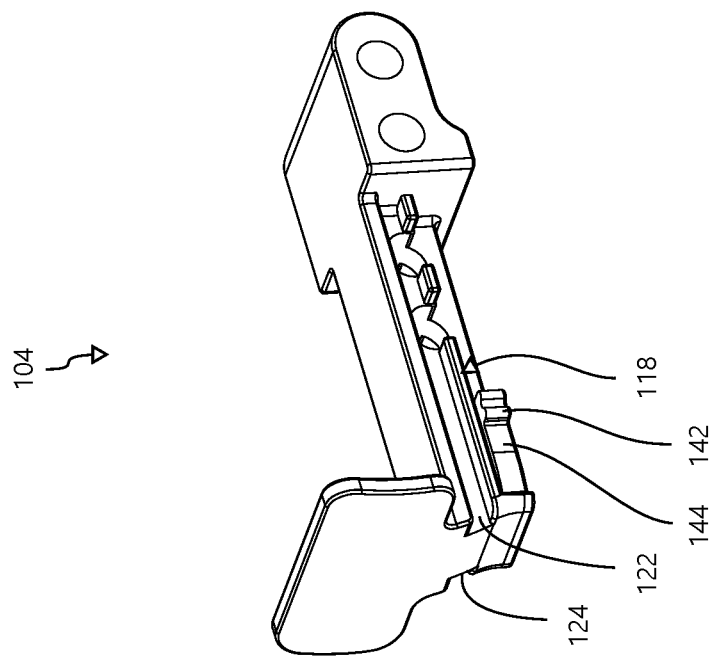

FIGS. 1 and 2 illustrate a first embodiment of a storage medium holder 100 according to the invention. The storage medium holder 100 comprises a base part 102 and a sliding part 104. The base part 102 is shown separately in a perspective view and a side view in FIGS. 4, 5, and the sliding part 104 is shown in FIGS. 6, 7.

The storage media holder 100 includes a holding portion 106 and a bite portion 108. The holding portion 106 is formed, on the part of the base portion 102, by a contact area 109 having a flatly formed contact surface 110, and on the part of the sliding portion 104, by a clamping area 112. The planar contact surface 110 is configured to support a storage medium, generally located in a protective case, so that the storage medium can assume the intended shape, generally planar.

The clamping region 112 has, as can be seen well in FIG. 2, a clamping surface 114 which is convex in shape with respect to the contact region 109. In the embodiment shown, the clamping surface 114 is generally cylindrical in shape, with the longitudinal axis of the curvature cylinder being substantially parallel to the contact surface 110. In this manner, a contact force can be uniformly applied along the cylinder axis from the clamping surface 114 to the contact surface 110 or to a storage medium (not shown) therebetween.

The bite portion 108 extends substantially perpendicular to the contact surface 110 along an axis A. For example, the angle that the contact surface 110 and the axis A make may be between 75° and 95°, preferably between 80° and 90°.

At the point where the contact surface 110 of the holding portion 106 merges into the bite portion 108, a concave shaped transition portion 115 is provided or is formed or shaped. This is designed in such a way that a storage medium, in particular an imaging plate, introduced into the region between the contact region 109 and the clamping portion 112 does not strike hard against a surface with the edge located at the front during the insertion process, but can slide off smoothly and thus, for example, damage to the edge of the storage medium—as could be the case, for example, with a comparatively sensitive imaging plate or the protective cover enclosing it—can be avoided.

The base part 102 has a first guide region 116 in the region of the bite portion 108, and the sliding part has a corresponding second guide region 118—see FIGS. 4 and 6. In the embodiment shown, the guide regions 116, 118 cooperate in a manner similar to a drawer guide: Two ledges 120 (only one ledge 120 is visible in the figures, see for example FIG. 4) are attached to the base part 102 in the first guide region 116, which ledges 120 are opposite each other and engage in grooves 122, 124 of the second guide region 118 of the sliding part 104. In the embodiment shown, the ledges 120 and the associated grooves 122, 124 are partially interrupted in order to create a space for a locking device described below on the one hand, and at the same time to create a guide through the groove ledge guide as far as possible over the entire length of the range of movement of the base part 102 and the sliding part 104.

In the embodiment shown, the groove ledge guide runs parallel to the longitudinal axis A of the bite portion 108, but this is not necessary: there could also be an angular offset or/and one or more interruptions between the longitudinal axis A and the groove ledge guide (not shown in the figures).

By means of the described groove ledge guide, a displaceability between the base part 102 and the sliding part 104 is realized. The sliding part 104 can thus be displaced along a sliding axis-here: parallel to the longitudinal axis A-relative to the base part 102. Thus, the storage medium holder 100 can be moved from an open position to a clamping position and vice versa.

The open position is shown in FIGS. 1 and 2. There, a gap is located between the contact surface 110 and the clamping surface 114, which allows easy insertion of the storage medium. Depending on the type of storage medium-imaging plate, memory sensor, memory chip, memory film, etc.—the distance may be suitably dimensioned for insertion.

Figure 3:
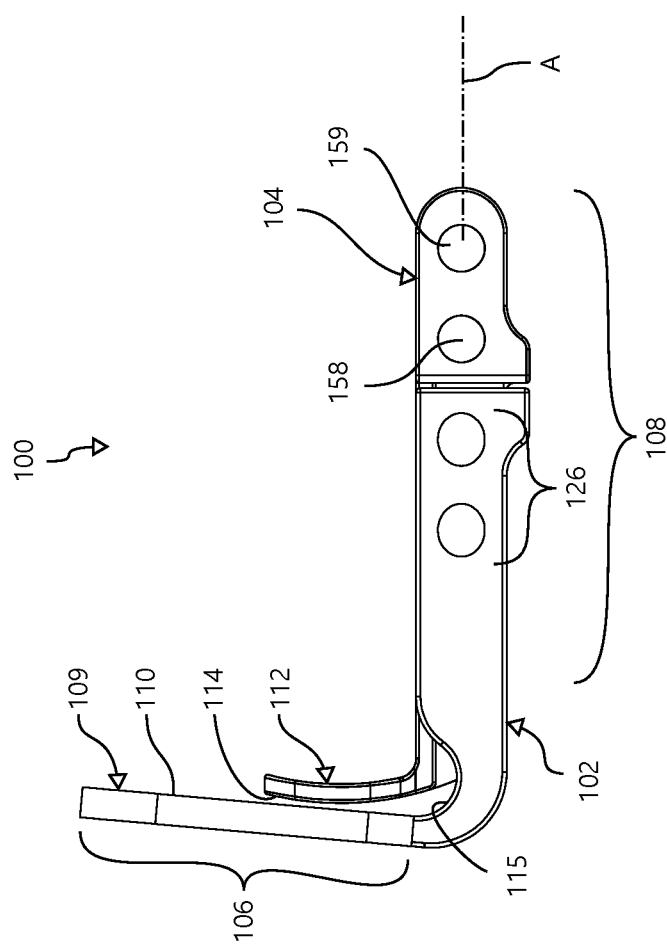
FIG. 3 a side view of the embodiment of FIG. 2 with the base part and sliding part in a clamped position.

In the clamping position, on the other hand, which is illustrated in FIG. 3, the sliding part 104 is maximally inserted into the base part 102. Accordingly, the distance between the contact surface 110 and the clamping surface 114 is such that the inserted storage medium is subjected to a contact force or contact pressure. A predetermined contact force is exerted on a storage medium located between the two surfaces in such a way that a clamping force is produced, in particular in a range from 1.8 N to 4.2 N, preferably in a range between 2.2 N and 3.4 N and particularly preferably in a range between 2.5 N and 3.0 N. On the one hand, this contact force causes the storage medium to contact the contact surface 110 and, on the other hand, to be secured against slipping or falling out due to the resulting clamping force.

In order to achieve the desired contact force and the resulting clamping force, the holding device 100 is adapted or can be adapted to a specific thickness of the storage medium and to the maximum contact force that can be applied thereto. Exemplary thicknesses of the imaging plates are between 200 μm and 1000 μm, in particular between 300 μm and 900 μm and, for example, at 340±40 μm or 760±80 μm for imaging plates and between 5 mm and 8 mm, in particular between 5.5 mm and 7.5 mm and, for example, at 6.4 mm for memory sensors.

In order to secure or lock the base part 102 and the sliding part 104 against each other against slipping in the clamping position, at least one locking region 126, 128 is provided on each of the base part 102 and the sliding part 104. The locking regions 126, 128 are each implemented by a pair of openings 130, 132/134, 136, here exemplarily implemented as bores, which are aligned with one another in the intended clamping position. In the embodiment shown, the openings 130-136 are cylindrical. However, other shapes are also possible, such as, for example, in a non-exhaustive list, with a square, triangular, trapezoidal or elliptical cross-section.

When the openings 130, 132 of the locking portion 126 of the base part 102 are aligned with the bores 134, 136 of the locking portion 128 of the sliding part 104, a locking device 152 (see FIG. 8) can be inserted, for example plugged, into the aligned recesses thus formed. The locking device may be, for example, a target or guide rod 150 on which a locking device 152 may be formed. Since the locking regions 126, 128 are arranged in pairs, spatial fixing of the target rod 150 can thus be achieved by simple means. However, this would also be possible alone by a suitable shaping of the openings as already mentioned (square, triangular, trapezoidal, elliptical, or the like) with only one aligned recess.

In an alternative embodiment, in addition to the locking feature just described, locking of the base part 102 to the sliding part 104 via the locking portions 126, 128 can be achieved via detents or the like. Such a locking device can be seen in FIGS. 4 and 5. In a lateral region-here in the embodiment example below the ledges 120-*a* detent surface 140 is provided on the base part 102. This may, for example, have individual protruding ribs, indentations or, for example, an undulating surface. The detent surface 140 corresponds with one or more detent cams 142 on the sliding member 104, and the shaping of the detent cam 142 cooperates with the surface shaping of the detent surface 140 to achieve the desired detent action. Additionally, the detent cam 142 may be of a elastic design. This can be seen in FIG. 6. The detent cam 142 is attached to the end of a spring arm 144, allowing it to move toward the surface of the detent surface 140 when sliding over the surface of the detent surface 140 when engaging a depression, and to swing away from the surface of the detent surface 140 when overcoming an elevation, overcoming the spring force of the spring arm 144.

FIG. 8 illustrates the above-described embodiment of a storage medium holder 100 in a perspective view in the clamped position, i.e., the sliding part 104 is fully inserted into the base part 102 along the sliding axis A. In this position, some relative locking of the base part 102 with the sliding part 104 is already realized by means of the locking device detent lugs 142/detent surface 140.

However, in order to achieve an absolutely secure locking of the two parts 102, 104, which are in principle displaceable relative to each other, for handling in the oral cavity of the patient, a locking device 152 attached to a target rod 150 can be used as already described above. Although the arrangement of the locking device 152 on the target rod 150 or the combination of the locking device 152 and the target rod 150 is advantageous with respect to the entire device, a locking device 152 can in principle also be used without a target rod 150.

As already indicated above, the locking device comprises at least one locking pin which is geometrically shaped such that it can be brought into engagement with at least one of the openings 130, 132/134, 136. In the embodiment example shown in FIG. 8, two cylindrical locking pins 154, 156 are provided which can be inserted into the openings 130, 132 of the locking area 126 of the base part 102 and subsequently also into the bores 134, 136 of the locking area 128 of the sliding part 104. As long as these locking pins 154, 156 remain in the bores of the locking areas 126, 128, a relative movement of the parts 102, 104 with respect to each other is not possible, so that even a storage medium located between the contact surface 110 and the clamping surface 114, such as an imaging plate (usually with a protective cover), can be securely held or clamped.

In addition, other openings 158, 159 are provided on the sliding portion 104 (see FIG. 3). For example, the opening 158 closer to the base part 102 may also be provided to receive a locking pin 154 to achieve locking of the base part 102 and the sliding part 104. The further opening 159, together with the opening 158, may allow the locking pins 154, 156 of the target rod 150 to be received without resulting in locking of the base part 102 and the sliding part 104.

Second Embodiment

Figure 10:
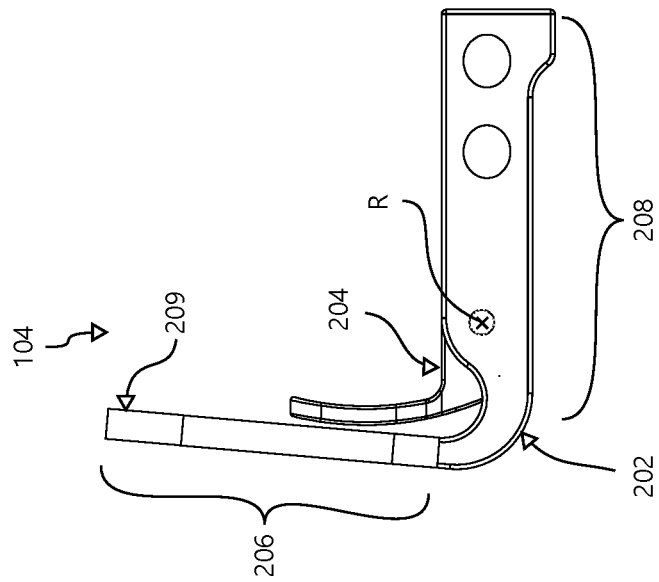
FIGS. 9, 10 side views of a second embodiment in open position and clamped position.
Figure 9:
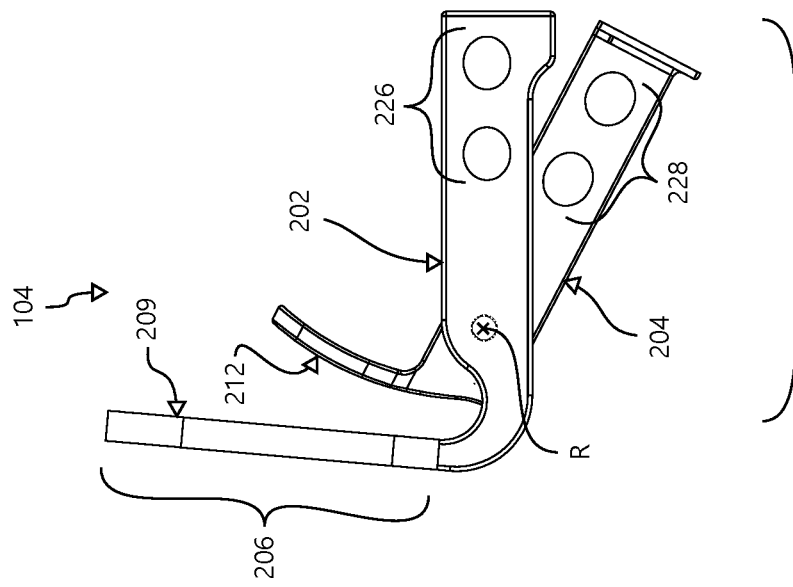

FIGS. 9 and 10 illustrate, in side views, a second embodiment of a storage medium holder 200. The storage medium holder 200 includes a base part 202 and a pivot part 204. FIG. 9 shows the storage medium holder 200 in an open position, and FIG. 10 shows the storage medium holder 200 in a clamped position.

In analogy to the storage medium holder 100 illustrated in FIGS. 1-8, the storage medium holder 200 of FIGS. 9 and 10 includes a holding portion 206 and a bite portion 208. In this regard, the storage medium holder 200 is constructed in a manner largely analogous to the storage medium holder 100 of FIGS. 1-8, so that no further description of the same or very similar features will be provided. Instead, reference numerals to which 100 has been added are used in the figures and in the description below for identical or very similar features.

In contrast to the storage medium holder 100 of FIGS. 1-8, in the storage medium holder 200 of FIGS. 9 and 10 the relative movement for a change between the open position of FIG. 9 and the clamped position of FIG. 10 is effected via a pivoting or rotating movement in which the pivoting part 204 rotates about an axis R. The axis may be structurally designed as a rotating or fixed axis, as a separate (third component) or as an integrally formed axis section on the base part 202 or the pivot part 204. Also, base part 202 and pivot part 204 may be fixedly connected to each other via the pivot axis. Alternatively, base part 202 and pivot part 204 may be insertable into each other in a certain rotational position with respect to each other—for example, in the open position—and connected to each other after a certain rotational angle.

Third Embodiment

Figure 12:
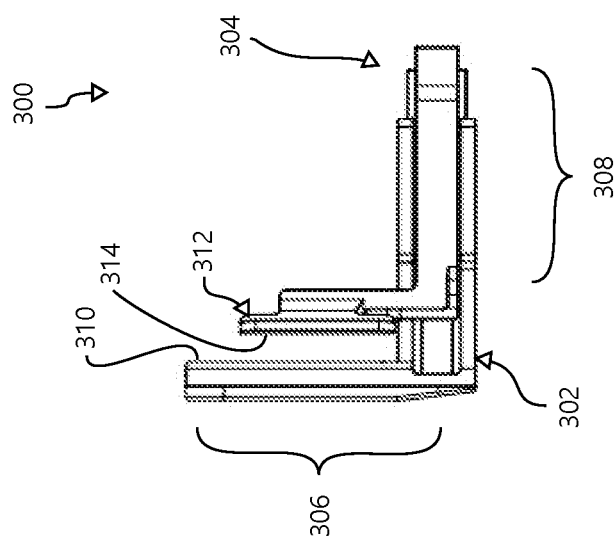
FIGS. 11 and 12 are a side view and a top view, respectively, of an embodiment of a storage medium holder in an open position.
Figure 11:
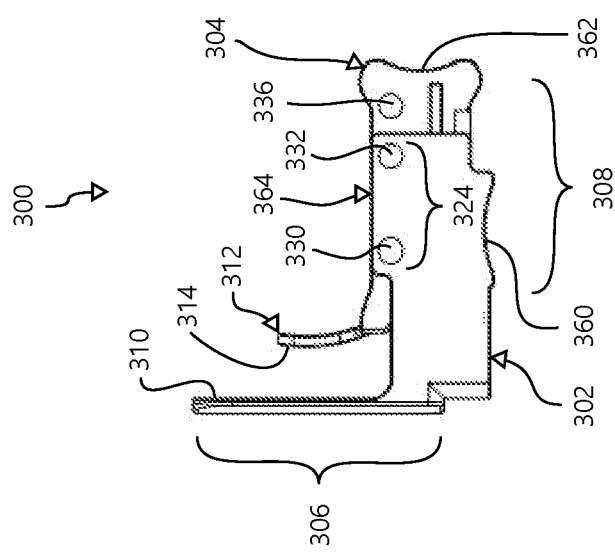

FIGS. 11 and 12 illustrate, in a side view and in a top view, a third embodiment of a storage medium holder 300. Also like the first embodiment, the storage medium holder 300 comprises a base part 302 and a sliding part 304. Due to the large number of identical or comparable features, the same will not be described again in order to avoid repetition. Instead, identical or comparable features are provided with reference signs to which-com-pared to the first embodiment example—200 has been added.

Briefly summarized, the storage medium holder 300 also includes a holding portion 306 having a planar abutment surface 310 on the base part 302 and a clamping region 312 having a convexly shaped clamping surface 314 on the sliding part 304. Similarly, a bite portion 308 is provided on the storage medium holder 300. An ergonomically shaped first portion 360 is provided on the bite portion 308 at the base part 302. This corresponds to a second ergonomically shaped region 362 formed on the face of the sliding portion 304.

To receive or hold a storage medium in the holding portion 306, an operator may grip the storage medium holder 300 with his left hand, for example, such that his middle finger is positioned in the first ergonomic region 360, his index finger is positioned opposite thereto on the upper surface 364 of the storage medium holder 300, and his thumb is positioned against the second ergonomic region 362. The operator can then insert the storage medium into the holding portion 306 with the right hand and, by pressing the thumb against the ergonomic region 362, apply the holding force necessary to adequately hold the storage medium (not shown in the figures) between the contact surface 310 and the clamping surface 314.

In a further difference to the embodiment of FIGS. 1-8, the contact surface 310 is not arranged centrally to the axis A along which the bite portion 308 extends and along which the sliding movement of the sliding part 304 relative to the base part 302 also takes place. The same applies to the clamping surface 314. Rather, the contact surface 310 and the clamping surface 314 are arranged laterally offset with respect to said longitudinal axis A. This arrangement is advantageous for storage media which have connecting lines for, for example, a voltage supply or for transmitting data. In this case, the storage medium, in particular a memory sensor, can be inserted into the holding portion 306 in such a way that these connecting lines can be inserted along the longitudinal axis A in the lower region of the bite portion 308, for example, into correspondingly attached cable clips or cable clamps (not shown). The lateral arrangement of contact surface 310 and clamping surface 314 provides sufficient space for the memory sensor's own cable management for this purpose.

In the same manner as the first embodiment, openings 330, 332 are provided in the base part 302 in the locking area 324 of the base part 302 as well as openings 334, 336 (in FIG. 11 only the opening 336 is visible) in the locking area of the sliding part 304. A target or guide rod 150 may be inserted into these openings 330-336 in the same manner as in the first embodiment to lock or lock the base part 302 and sliding part 304 together in a clamping position.

Additionally, or alternatively, this locking or locking in the clamping position can also be realized by a latching mechanism between base part 302 and sliding part 304 as already described in the first embodiment (not shown in FIGS. 11 and 12). This latching may be releasable again by suitable controls of the latching mechanism for an operator, so that base part 302 and sliding part 304 are separable, for example, for sterilization.

The invention claimed is:

1. A device configured to hold an imaging plate in the oral cavity of a patient for at least one X-ray exposure, the device comprising:
   a holding portion;
   a first part with an abutment region for the imaging plate;
   a second part with a clamping region for the imaging plate; and
   a bite portion, wherein the bite portion comprises
   a first guiding or/and joint region and a first locking region, and
   a second guiding or/and joint region corresponding to the first guiding or/and joint region and a second locking region,
   wherein said abutment region and said clamping region cooperate to form a retaining portion, said first and second guide or/and joint regions cooperate such that said first part and said second part are movable relative to each other between an open position and a clamping position, and in said clamping position, said abutment region and said clamping region are configured to exert a clamping force on an imaging plate located therebetween, said first part and said second part being lockable relative to each other in said clamping position via cooperation of said first and second locking portions, and
   wherein a planar clamping region has a convex-shaped surface with respect to the imaging plate.

2. The device according to claim 1, wherein the abutment region comprises an abutment surface configured for flat support of an imaging plate.

3. The device according to claim 1, wherein a contact surface is arranged or/and adjustable at an angle between 75° and 95° with respect to the bite portion.

4. The device according to claim 1, wherein a holding section is adjustable and lockable in its inclination with respect to the bite portion.

5. The device according to claim 4, wherein the inclination is arranged or/and adjustable at an angle between 75° and 95° to the bite portion.

6. The device according to claim 1, wherein recesses corresponding to one another are arranged on the first part and the second part in the locking area in such a way that a locking device can be inserted through the recesses and thus the first part and the second part are configured to be locked to one another.

7. The device according to claim 1, wherein the guide region comprises a ledge guide configured such that the abutment region and the clamping portion are displaceable relative to each other from an open position to a closed position, and thus the clamping region is configured to exert the clamping force to the abutment region.

8. The device according to claim 1, wherein a joint portion has an axis of rotation on the first or the second part and a bearing corresponding thereto on the other part.

9. The device according to claim 8, wherein the axis of rotation is arranged such that the abutment region and the clamping portion are configured to perform a pivoting movement relative to each other.

10. The device according to claim 1, wherein between the abutment region and the clamping portion there is a distance dimensioned such that in the open position the imaging plate can be inserted between the abutment region and the clamping portion and in the clamping position a predetermined clamping force is exerted on the imaging plate dimensioned such that during handling of the device the imaging plate can be clamped.

11. The device according to claim 1, wherein the abutment region has a concave-shaped transition section at or/and formed in its lower region.

12. The device according to claim 1, wherein a contact surface is arranged or/and adjustable at an angle between 80° and 90° with respect to the bite portion.

13. The device according to claim 4, wherein the inclination is arranged or/and adjustable at an angle between 80° and 90° to the bite portion.

14. A device configured to hold an imaging plate in the oral cavity of a patient for at least one X-ray exposure, the device comprising:
- a holding portion;
- a first part with an abutment region for the imaging plate;
- a second part with a clamping region for the imaging plate; and
- a bite portion, wherein the bite portion comprises
- a first guiding or/and joint region and a first locking region, and
- a second guiding or/and joint region corresponding to the first guiding or/and joint region and a second locking region,
  - wherein said abutment region and said clamping region cooperate to form a retaining portion, said first and second guide or/and joint regions cooperate such that said first part and said second part are movable relative to each other between an open position and a clamping position, and in said clamping position, said abutment region and said clamping region are configured to exert a clamping force on an imaging plate located therebetween, said first part and said second part being lockable relative to each other in said clamping position via cooperation of said first and second locking portions, and
  - wherein a joint portion has an axis of rotation on the first or the second part and a bearing corresponding thereto on the other part.

15. A device configured to hold an imaging plate in the oral cavity of a patient for at least one X-ray exposure, the device comprising:
- a holding portion;
- a first part with an abutment region for the imaging plate;
- a second part with a clamping region for the imaging plate; and
- a bite portion, wherein the bite portion comprises
- a first guiding or/and joint region and a first locking region, and
- a second guiding or/and joint region corresponding to the first guiding or/and joint region and a second locking region,
  - wherein said abutment region and said clamping region cooperate to form a retaining portion, said first and second guide or/and joint regions cooperate such that said first part and said second part are movable relative to each other between an open position and a clamping position, and in said clamping position, said abutment region and said clamping region are configured to exert a clamping force on an imaging plate located therebetween, said first part and said second part being lockable relative to each other in said clamping position via cooperation of said first and second locking portions, and
  - wherein the abutment region has a concave-shaped transition section at or/and formed in its lower region.

* * * * *